United States Patent [19]

Shults et al.

[11] Patent Number: 4,994,167

[45] Date of Patent: Feb. 19, 1991

[54] BIOLOGICAL FLUID MEASURING DEVICE

[75] Inventors: Mark G. Shults, Madison; Christopher C. Capelli, Kenosha; Stuart J. Updike, Madison, all of Wis.

[73] Assignee: Markwell Medical Institute, Inc., Racine, Wis.

[21] Appl. No.: 216,683

[22] Filed: Jul. 7, 1988

Related U.S. Application Data

[63] Continuation-in-part of Ser. No. 852,343, Apr. 15, 1986, abandoned, which is a continuation-in-part of Ser. No. 774,330, Sep. 10, 1985, abandoned.

[51] Int. Cl.$^5$ .......................................... G01N 27/404
[52] U.S. Cl. ................................ 204/403; 204/412; 204/415
[58] Field of Search ............... 204/403, 412, 415, 418; 435/817; 128/635

[56] References Cited

U.S. PATENT DOCUMENTS

| | | | |
|---|---|---|---|
| 3,933,593 | 1/1976 | Sternberg | 435/291 |
| 3,966,580 | 6/1976 | Janata et al. | 204/195 B |
| 3,979,274 | 9/1976 | Newman | 204/403 |
| 4,040,908 | 8/1977 | Clark | 435/291 |
| 4,073,713 | 2/1978 | Newman | 204/195 B |
| 4,151,049 | 4/1979 | Janata | 204/1 T |
| 4,172,770 | 10/1979 | Semersky et al. | 435/291 |
| 4,240,889 | 12/1980 | Yoda et al. | 204/195 B |
| 4,290,431 | 9/1981 | Herbert et al. | 128/635 |
| 4,303,076 | 12/1981 | Danek | 128/635 |
| 4,311,151 | 1/1982 | Hagihara | 128/635 |
| 4,388,166 | 6/1983 | Suzuki et al. | 204/403 |
| 4,404,066 | 9/1983 | Johnson | 104/1 T |
| 4,418,148 | 11/1983 | Oberhardt | 435/179 |
| 4,439,196 | 3/1984 | Higuchi | 604/890 |
| 4,454,007 | 6/1984 | Pace | 204/1 T |
| 4,475,916 | 10/1984 | Himmelstein | 604/890 |
| 4,525,410 | 7/1985 | Pace | 204/412 |
| 4,534,355 | 8/1985 | Potter | 128/635 |

FOREIGN PATENT DOCUMENTS

1442303 7/1976 United Kingdom ................ 204/403

OTHER PUBLICATIONS

Ko, Wen H., Implantable Sensors for Closed Loop Prosthetic Systems, Ch. 12, 167–175, Futura Publishing Co. (1985).

ASTM E 96, Standard Test Methods for Water Vapor Transmission of Materials, Annual Book of ASTM Standards, 04.06, 776–785, (1986).

Shichiri et al., "Wearable Artificial Endocrine Pancreas with Needle-Type Glucose Sensor", The Lancet, 1129–1131 (Nov. 1982).

Muir et al., J. Biomed. Mater. Res., 5, 425–445 (1971).

Primary Examiner—Nam X. Nguyen
Attorney, Agent, or Firm—Olson & Hierl

[57] ABSTRACT

A biological fluid measuring device for determining the presence and the amounts of substances in a biological fluid without the need for dilution of the fluid comprises a main housing including electronic circuit means and at least one electrode, and a cartridge having a membrane. The cartridge is removably mounted on the housing and the membrane is maintained operably associated by osmotic pressure with the electrode. The cartridge also includes means for protecting the membrane when the device is not in use. An enzyme electrode is also disclosed comprising a multilayered homogeneous monolithic membrane and an intermediate water-swellable coating.

72 Claims, 3 Drawing Sheets

FIG_1

FIG_2

BIOLOGICAL FLUID MEASURING DEVICE

CROSS REFERENCE TO RELATED APPLICATION

This application is a continuation-in-part of pending application Ser. No. 852,343 filed Apr. 15, 1986, which is a continuation-in-part of pending application Ser. No. 774,330 filed Sept. 10, 1985 and entitled "Enzyme Electrode" all abandoned.

TECHNICAL FIELD

The present invention relates to devices having replaceable membranes which cooperate with an electrode assembly to determine the amount of a substance in a biological fluid.

BACKGROUND OF THE INVENTION

The continuous measurement of substances in biological fluids is of interest in the study and control of metabolic disorders. Electrode systems have been developed for this purpose whereby an enzyme-catalyzed reaction is monitored by an electrochemical sensor. In such electrode systems, the electrochemical sensor comprises an electrode with potentiometric or amperometric function in close contact with a thin layer containing an enzyme in dissolved or insoluble form. The thin layer may also include a co-enzyme.

In conventional practice, a semipermeable membrane separates the thin layer of the electrode containing the enzyme from the sample of biological fluid that includes the substance to be measured. The electrochemical sensor measures the concentration of the substance involved in the enzyme reaction. For example, the concentration of a co-enzyme or a reaction product can be determined. This concentration may be related to the substrate concentration in the sample by its stoichiometric relationship and by calibration of the electrode system.

A number of enzyme electrodes have been developed, and the operation of those electrodes varies depending on the nature of the enzyme reaction and the particular substance being measured. For example, enzyme electrodes include those that measure: (1) a reactant or product of the enzyme reaction; (2) the consumption of a co-enzyme based on the decrease of its initial concentration and (3) the amount of the reduced or oxidized form of a co-enzyme produced during the enzyme reaction.

The operation of a particular enzyme electrode depends on a number of parameters including diffusion processes, kinetics of the enzyme reaction and the type of electrochemical sensor. In particular, the operation of the electrode can be affected by the diffusion of substances through the semipermeable membrane.

Electrode systems that include enzymes have been used to convert amperometrically inactive substances into reaction products which are amperometrically active. Specifically, in the analysis of blood for glucose content, glucose (which is relatively inactive amperometrically) may be catalytically covered by the enzyme glucose oxidase into the presence of oxygen and water to gluconic acid and hydrogen peroxide. Hydrogen peroxide is anodically active and produces a current which is proportional to the concentration of hydrogen peroxide in the blood sample and thus to the concentration of glucose in the sample.

In a sample of undiluted whole blood, however, a molar excess of plasma glucose is present relative to the amount of plasma oxygen. As a result, if a semipermeable membrane is not included over the enzyme, the concentration of glucose in the sample relative to the concentration of oxygen will be so high that the glucose oxidase-catalyzed reaction of glucose and oxygen to gluconic acid and hydrogen peroxide will be oxygen limited.

The effect of an oxygen limited reaction is that the range of glucose concentrations that can be measured with such an electrode is very limited. In particular, linearity is not achieved above minimal concentrations of glucose. In a clinical setting, linear glucose levels must be obtained at glucose concentrations of at least up to about 500 milligrams per deciliter (mg/dl). Without a semipermeable membrane over the enzyme, linear glucose levels can be obtained only up to about 40 mg/dl. Thus, the purpose of the membrane over the enzyme in a glucose sensing electrode system is to limit the amount of glucose that passes or diffuses through the membrane. This extends the upper limit of linearity of glucose measurement from a low value without the membrane to a high value with the membrane.

The two fundamental diffusion processes by which a semipermeable membrane can limit the amount of a substance that passes therethrough are diffusion through the semipermeable membrane as a monolithic, homogeneous structure and diffusion through the semipermeable membrane as a porous structure. The processes of diffusion of substances through these different types of membranes differ considerably.

A semipermeable membrane can comprise a porous structure consisting of a relatively impermeable matrix that includes a plurality of "microholes" or pores of molecular dimensions. Transfer through these membranes is primarily due to passage of substances through the pores. In other words, the membrane acts as a microporous barrier or sieve.

Examples of materials that may be used to form such membranes include polyethylene, polyvinylchloride, tetrafluoroethylene, polypropylene, cellophane, polyacrylamide, cellulose acetate, polymethyl methacrylate, silicone polymers, polycarbonate, cuprophane and collagen.

Selectivity in such a membrane can be explained on the basis of the molecular size of the diffusing substances. For substances much smaller than the diameter of the pores, passage of the substance through the membrane is relatively unimpeded. As the effective molecular diameter of the substance approaches the diameter of the pore, the pore will exert a drag on the diffusing substance, reducing its permeability to a value lower than that expected on the basis of the membrane porosity. If the molecules of the substance are too large, they will not pass through the membrane at all.

Since transfer is due primarily to passage of the substance through pores, the permeability is directly related to the size of the pores and to the molecular volume of the diffusing substance. As a result, there is little selectivity in the separation of two chemically or structurally related molecules, except when their molecular size is approximately the same as the size of the pore. When this occurs, there is the possibility that forces acting between the substance and the surface of the pore channel may influence the rate of transfer.

Also, the upper size limit to diffusion will be determined by the largest pore diameter, and the overall diffusion rate will depend on the total number of pores for movement of the substance.

Passage of a substance through a monolithic, homogeneous membrane, on the other hand, depends upon selective dissolution and diffusion of the substance as a solute through a solid, non-porous film. As used herein, the term "monolithic" means substantially non-porous and having a generally unbroken surface. The term "homogeneous", with reference to a membrane, means having substantially uniform characteristics from one side of the membrane to the other. However, a membrane may have heterogeneous structural domains, for example, created by using block copolymers, and still be characterized functionally as homogeneous with respect to its dependence upon dissolution rather than sieving to effect separation of substances. A monolithic membrane can thus be used to selectively separate components of a solution on the basis of properties other than the size, shape and density of the diffusing substances. The membrane acts as a barrier because of the preferential diffusion therethrough of some substance (a solute).

Despite advances in membrane technology, devices that include semipermeable membranes which have been used to detect and measure the presence of a substance in a biological fluid have generally been restricted to laboratory environments. This is because the devices are generally large and complex and require extensive training to operate. In addition, these devices have been somewhat limited because of the difficulty in replacing a membrane used with the electrode.

A need exists for an improved device that selectively measures the presence and the amounts of particular substances in biological fluids. Such a device should accurately measure the amount of substance in a sample without dilution or pretreatment of the sample. In addition, a basis for selecting appropriate membrane materials for use in such devices is needed. The device should also be easy to use and provide a means for replacing the membrane a necessary.

SUMMARY OF THE INVENTION

The present invention relates to a biological fluid measuring device which permits rapid and accurate determination and measurement of the amount of a particular substance in a biological fluid such as blood.

Generally, the device includes a main housing carrying electronic circuit means and at least one electrode. In a preferred embodiment, at least two electrodes are carried by the housing. A disposable cartridge is removably mounted on the housing. It is, of course, possible to design a device wherein one electrode is carried by the housing and a second electrode is carried by another component of the device, as by the cartridge. For ease of description, however, the present device will be described as including at least two electrodes carried by the housing.

The cartridge includes a membrane which is operably associated with the electrodes when the cartridge is mounted on the housing. The cartridge also includes means for protecting the membrane from the ambient surroundings when the device is not in use. In addition, means is provided for maintaining the membrane in operative contact with the electrodes by osmotic pressure.

In a preferred embodiment, the housing includes an instrument case having an upper portion and a lower portion which together define a cavity. The electronic circuit is contained within the cavity. The electrode is carried by a post which extends upwardly from a base surface defined by the upper portion of the case.

The cartridge preferably includes a body portion which is releasably mounted on the upper portion of the case and a cover which is movably mounted as by a hinge on the body portion. The body portion preferably defines a sidewall which together with the membrane defines a well. The well receives the biological fluid such as a droplet of blood. Because of the particular design of the present invention, the well can be particularly small thereby minimizing the amount of biological fluid sample needed for analysis. In the case of blood, this minimizes both the emotional and physical trauma to the patient.

The body portion preferably includes a collar which extends about the post such that, when the cartridge is mounted on the case, the membrane is placed in contact with the electrodes and is stretched over the surface of the electrodes. This ensures good operative contact between the electrodes and the membrane at the electrode-membrane interface.

In a preferred embodiment, a liquid means for maintaining the membrane in operative association with the electrodes at the electrode-membrane interface by osmotic pressure is received in the well above and in contact with the membrane. This liquid includes an osmotic agent which does not permeate the membrane and is capable of applying an osmotic pressure across the membrane. This osmotic pressure ensures constant stable proximity of the membrane to the electrode to maintain stable contact during use, and thus enhances sensor stability. In effect, the osmotic pressure maintains stability of the diffusion path from sample to the electrode by gently forcing the gel-like membrane to maintain contact with the electrode surface. This prevents the accumulation of additional unwanted electrolyte solution between the membrane and the electrode surface. The osmotic pressure effect withdraws solvent molecules from the hydrated membrane and from the electrode-membrane interface that might otherwise mechanically destabilize the diffusion path from sample to electrode surface. This diffusion path must maintain constant length in order for the sensor to exhibit analytical stability.

The electrodes, the supporting structure for the electrodes such as the post, the pressure means and the membrane together form an electrode assembly. The membrane is a multilayered structure including layers formed of materials such as polyethylene, polyvinylchloride, tetrafluorethylene, polypropylene, cellophane, polyacrylamide, polymethyl methacrylate, silicone polymers, polycarbonate, cuprophane, collagen, polyurethanes and block copolymers thereof. The membrane prevents direct contact of the fluid sample with the electrodes, but permits selected substances of the fluid to pass through the membrane for electrochemical reaction with the electrodes. To ensure electrochemical reaction, the surface of the membrane layer nearest the electrode is preferably coated with a waterswellable film to maintain electrolyte at the electrode-membrane interface, and thereby improve the sensitivity of the measurement.

In a preferred embodiment, the membrane is a semipermeable multilayered membrane having at least one layer formed of a nonporous block copolymer having hydrophobic segments and hydrophilic segments that limits the amount of a substance passing therethrough and a second layer including an enzyme that reacts with the substance to form a product.

In a more preferred embodiment, the electrode assembly comprises an electrode, a first (outer) layer of a block copolymer that limits the amount of a hydrophilic substance passing therethrough, a second (intermediate) layer of a block copolymer including an enzyme bound to the first layer and a third (inner) layer of a block copolymer bound to the second layer and covering the surface of the electrode. The third layer is permeable to relatively low molecular weight substances, such as hydrogen peroxide, but restricts the passage of higher molecular weight substances.

In a particularly preferred embodiment, the unbound surface of the third (inner) layer is coated with a semipermeable, substantially solid water-swellable gel-like film. The film comprises the aqueous reaction product of a polyurethane having anionic carboxyl functional groups and non-ionic hydrophilic polyether groups crosslinked in the presence of polyvinylpyrrolidone. The coating, which preferably has a dry film thickness of about 0.1 mil to about 0.5 mil, enhances and maintains the selectivity of the molecular separation of the inner layer and thereby improves the sensitivity of the measured amount of product.

The preferred polymers which form the above-described membrane layers and the coating are selected and based on permeability and water swelling. An accepted industry test procedure for determining the permeability of a coating or membrane is ASTM E 96 which measures the moisture-vapor transmission rate of a material. (American Society for Testing and Materials, Philadelphia, PA).

As used herein, the moisture-vapor transmission rate (MVTR) of a membrane material is expressed in grams per square meter per 24 hours and is one means of defining the water resistance of a material.

The MVTR of a material may be expressed by the equation:

$$MVTR = \frac{Q}{at}$$

wherein the letter "Q" represents the amount of water vapor (in grams) that permeates the film; the letter "a" represents the film area (in square centimeters) and the letter "t" represents the time (in hours at a designated thickness). This value can be converted to grams of water per square meters per 24 hours. The MVTR values identified herein are for membranes that are about 1 mil thick.

The MVTR of the first (outer) layer described herein should be greater than about 4,000 grams per square meter per 24 hours, preferably greater than about 5,000 grams per square meter per 24 hours.

The MVTR of the third (inner) layer of the assembly should be from about 500 to about 4,000 grams per square meter per 24 hours, preferably from 1,000 to about 3,500 grams per square meter per 24 hours.

It will, of course, be understood that the above MVTR values for each layer can be varied or optimized depending on the substance to be measured and the enzyme that is employed.

In a preferred embodiment, the enzyme is glucose oxidase and the substance to be measured is glucose. The amount of glucose, for example, in an aliquot of undiluted whole blood, is determined by measuring the amount of hydrogen peroxide produced during the oxidation of glucose to gluconic acid by the enzyme.

Preferred polymers for the membrane layers may also be selected by studying water uptake or the swelling of the polymer. This is normally measured by soaking the polymer sample in water at a controlled temperature and exposure conditions until equilibrium is achieved followed by rapid drying of surface water and weighing of the polymer sample. Subtracting the dry weight from the swelled weight and then dividing by the dry weight and multiplying the value obtained by 100 provides the swell rate as a percent of dry weight. The swell rate of the first (outer) layer described herein should be greater than about 5 percent and preferably greater than about 10 percent. The swell rate of the third (inner) layer should be less than about 5 percent preferably less than about 3 percent.

The swell rate of the coating should be greater than about 5 percent and preferably greater than about 10 percent.

The present invention, however, is not limited to the measurement of glucose concentrations, and other enzyme-substrate systems can be used. Examples of other enzymes include galactose oxidase, uricase, cholesterol oxidase, alcohol oxidase, lactose oxidase, L-amino acid oxidase, D-amino acid oxidase, xanthine oxidase and ascorbic acid oxidase.

Nonetheless, to demonstrate the improvement of this invention over other membrane systems, the invention will be described in terms of measuring glucose concentrations based on the production of hydrogen peroxide by the action of glucose oxidase.

The membrane systems currently available are based on semipermeable membranes with microholes or pores. With these membranes there is little selectivity in the separation of substances that are rather close in size, except when the molecular diameters of the substances approach the diameters of the pores. When this occurs, forces between the substance and the surface of the pore channel may influence the rate of transfer.

The layers of the preferred multilayered membrane described herein each comprise homogeneous, monolithic membranes and differ in composition, structure and operation from conventional microporous membranes. This represents a substantial improvement over current membrane systems in terms of ease of manufacturing, lifetime of enzyme activity, and the ability to measure the concentrations of substances in undiluted samples.

In addition, the water-swellable coating on the layer of the membrane closest to the electrode represents a substantial improvement in sensor sensitivity by maintaining electrolyte in the electrolyte space at the membrane-electrode interface. This improvement also provides a more stable operation of the device by overcoming electrode start-up problems and drifting problems caused by inadequate electrolyte and the excessive hydrophobicity of the interface environment. Also, by coating the membrane in the above manner, the yield of usable membrane manufactured increases.

Thus, the sensitivity of the device of this invention is improved by the use of a multilayered membrane having the unbound surface of its inner layer coated intermediate to and covering the electrode and by maintaining the membrane in contact with the electrode by osmotic pressure during use. This improvement represents a substantial advantage over current membrane devices in terms of sensor sensitivity, stability of operation, overcoming electrode start-up problems and overcoming interference from mechanical or osmotic disturbances at the electrode-membrane interface.

In summary, passage of substances through the membranes described herein depends upon dissolution and diffusion of the substance through a solid, non-porous film. Components of a solution can be separated on the basis of properties other than the size, shape and density of the diffusing substance.

DETAILED DESCRIPTION OF THE INVENTION

The present invention relates to a biological fluid measuring device which permits rapid and accurate measurement of the amount of particular substance in a biological fluid. One particular use of the present invention is to determine the level of glucose in blood using only a small sample. This is a particularly important measurement for individuals having diabetes, and the device is a substantial development over devices that are now being used by individuals with diabetes to determine glucose levels.

Figure 1:
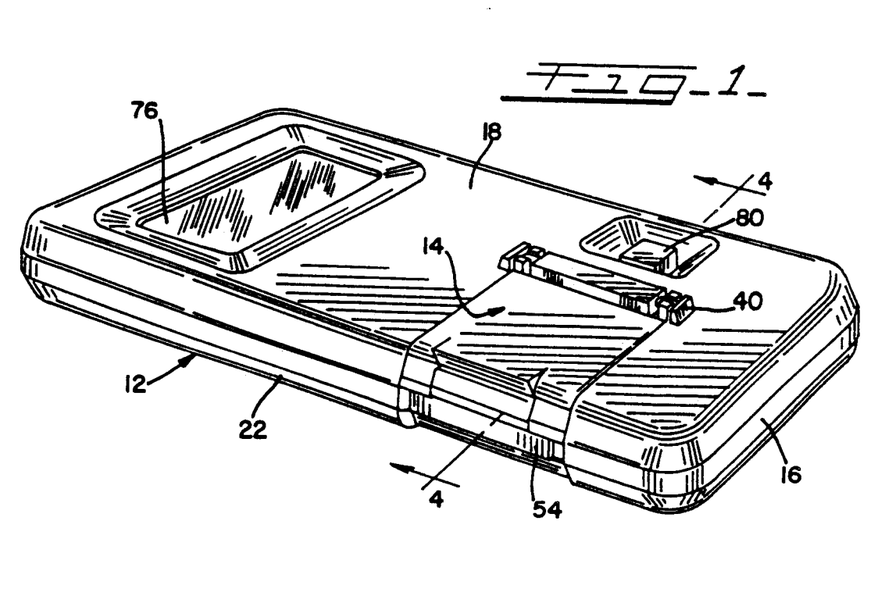
FIG. 1 is a perspective view of biological fluid measuring device of the present invention showing a cartridge received on a housing.
Figure 2:
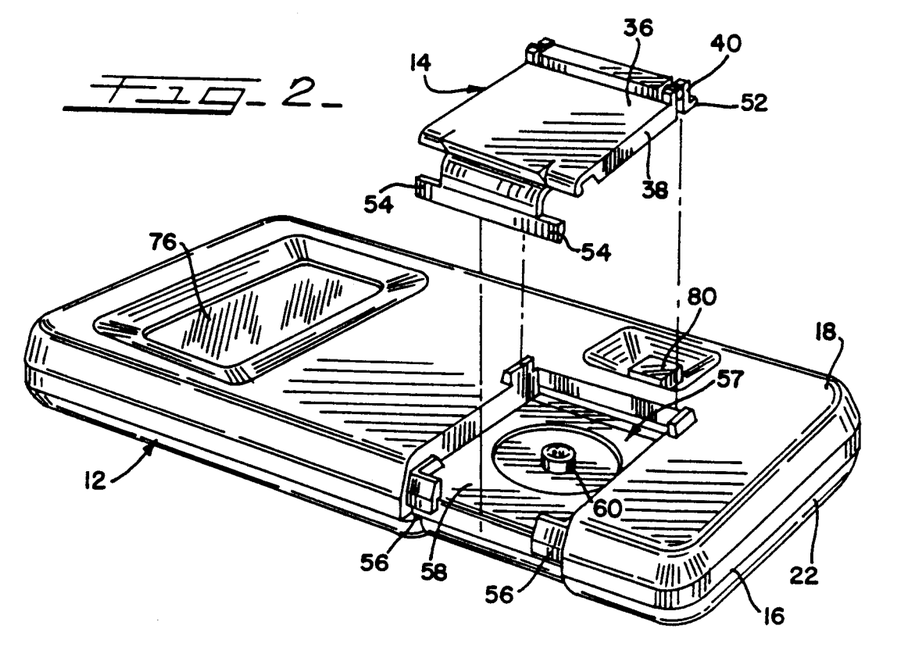
FIG. 2 is an exploded perspective view of the device of FIG. 1 showing the cartridge above and separated from the housing.

Referring to FIGS. 1 and 2, the measuring device comprises a main housing 12 and a cartridge 14 which is removably mounted on the housing (see FIG. 2). This permits the cartridge 14, which can be made disposable, to be easily replaced as needed. The construction of the cartridge will be described in detail with reference to FIGS. 4 and 4a. The housing 12 includes a case 16 having an upper portion 18 and a lower portion 22. The upper portion 18 and lower portion 22 are connected together by any particular fastening means such as several screws which are not shown.

Figure 3:
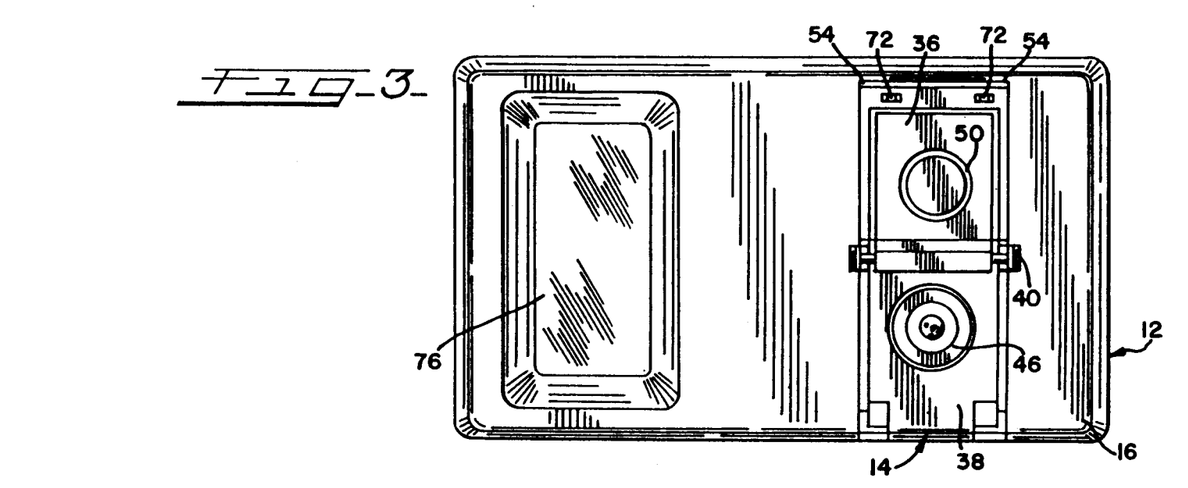
FIG. 3 is a top plan view of the device of FIG. 1 showing the cover of the cartridge open and the membrane exposed.
Figure 4:
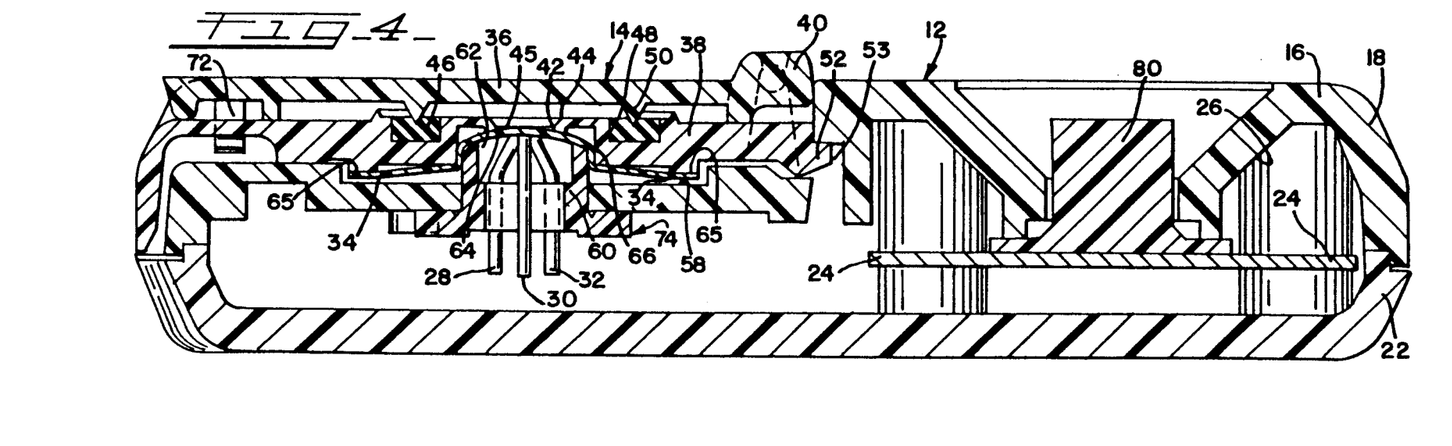
FIG. 4 is a side elevational view taken in section along the plane 4—4 of FIG. 1.

Referring also to FIGS. 3 and 4, the main housing 12 also includes electronic circuit means which can be carried in part on a circuit board 24. The electronic circuit means is preferably maintained in a cavity 26 which is defined by the case 16. The housing also includes at least one electrode. In the embodiment shown in FIG. 4, three electrodes 28, 30 and 32 are shown.

The operation of these electrodes is discussed in more detail below. The cartridge 14 includes a membrane 34 which is operably associated with the electrodes 28, 30 and 32 when the cartridge is removably mounted on the housing 12. In addition, the cartridge 14 can include means for maintaining osmotic pressure across the membrane 34 during use as also discussed in more detail below. The cartridge 14 also includes means for protecting the membrane when not in use. The protection means is preferably a cover 36 which is movably mounted on a body portion 38 of the cartridge 14. Alternatively, the cover 36 may be mounted on the case 16. In the illustrated embodiment, the cover 36 is movably mounted on the body portion 38 by a hinge assembly 40.

Generally, the cover 36 has a first position such as shown in FIGS. 1 and 4 in which it protects the membrane 34 and a second position such as shown in FIG. 3 which permits access to the membrane. Access to the membrane 34 is necessary to place the biological fluid sample on the membrane for analysis.

Figures 4A, 5:
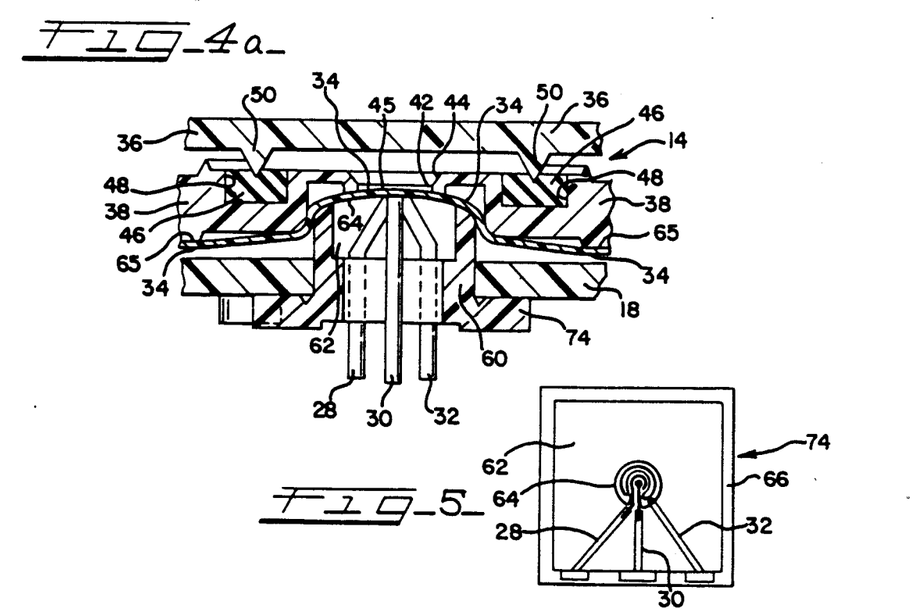
FIG. 4a is an enlarged view of the portion of FIG. 4 that is outlined in phantom.
FIG. 5 is a top plan view of a second embodiment of the electrode assembly.

As is more clearly shown in FIG. 4a (which is an enlarged view of the area outlined in phantom in FIG. 4), the body portion preferably defines an opening having a sidewall 42 which together with a portion of the membrane 34 defines a well 44 having a bottom 45. The bottom 45 of the well is defined at least in part by the membrane 34. For use, a liquid comprising an osmotic agent is received in the well 44 above and in contact with the membrane 34 in an amount sufficient to apply osmotic pressure across the membrane. The biological fluid sample is then placed in the well 44 for analysis.

An osmotic pressure of about 30 to about 90 millimeters, preferably about 70 millimeters, mercury (Hg) column height is exerted across the membrane at ambient room temperature.

Generally, the sidewall 42 defines an opening of less than 4 millimeters in diameter and the well 44 has the depth of less than 2 millimeters. As a result, the well has a volume of less than about 0.1 to about 0.2 cubic centimeters. This substantially minimizes the size of the biological fluid sample necessary for analysis down to sample sizes as small as about five microliters. Because the size of the sample can be particularly small, compensation for temperature changes during analysis which was often necessary with previous devices can be avoided.

For purposes of providing osmotic pressure across the membrane, prior to placing the biological fluid sample in the well 44, the surface of the membrane is first "cleaned" by blotting with an absorbent tissue. Then a drop of aqueous buffered cleaning and storage solution containing an osmotic agent is placed in the sample well. Preferably, the osmotic agent is a water-soluble nonionic polymer that is substantially solid at room temperature. Suitable osmotic agents have a weight average molecular weight of between over about 800 and about 20,000 molecular weight, preferably between about 1,500 and about 15,000, more preferably between about 3,000 and about 12,000. A particularly preferred aqueous cleaning and storage solution applies an osmotic pressure across the membrane of about 70 millimeters mercury column height at ambient room temperature and pressure. The volume of this liquid pressure means present in the well 44 is substantially minuscule. Nevertheless, the liquid received in the well 44 and in contact with the membrane 34 during storage or storage/use, enhances the measuring sensitivity and stability of the electrodes 28, 30 and 32 by 1) holding the membrane 34 against the electrodes 28, 30 and 32 by a relatively consistent osmotic pressure thereby maintaining optimal and stable contact at the electrode-membrane interface 64.

A preferred liquid pressure means comprises, as the osmotic agent, a homopolymer of polyvinylpyrrolidone dissolved at about 4 weight percent (about 4 millimolar) in water. An exemplary homopolymer is sold under the trademark BASF K-17PF by BASF Wyandotte Corporation (Parsippany, NJ) which is stated to have a number average molecular weight of about 2,500. Each millimole of concentration difference applies about 17 millimeters Hg column height pressure, so the foregoing liquid pressure means prepared from BASF K-17PF applies about 70 millimeters Hg column height pressure across the membrane.

Alternatively, a copolymer of N-vinylpyrrolidone and vinyl acetate or like water-soluble copolymer of N-vinylpyrrolidone can be used.

Other suitable osmotic agents include water-soluble linear ethylene oxide polymers, such as polyethylene glycols having a terminal hydroxyl group or terminal methoxy group having a weight average molecular weight distribution above about 800 to about 20,000, preferably about 900 to about 4,000 and being substantially solid at ambient room temperature.

Exemplary polyethylene glycols are commercially sold under the family trademark CARBOWAX as a PEG and MPEG series by Union Carbide Corporation, Industrial Chemicals Division (Danbury, CT). A detailed description of the properties of these polymers can be found in the *CARBOWAX Polyethylene Glycols*, Product Information Bulletin F-4772M, published in 1986 by the Union Carbide Industrials Chemical Division, the disclosures of which are incorporated herein by reference. Particularly preferred is CARBOWAX 3350, a solid polyethylene glycol having a molecular weight average distribution of about 3000 to about 3700, a melting point of about 54 to about 58 degrees C. (about 129.2 to about 136.4 degrees F.) and a water solubility of about 67 weight percent at 20 degrees C. (about 68 degrees F.).

The protection means of the cartridge 14 preferably also includes means for sealing the well 44 and hence the operative portion of the membrane 34 at the bottom 45 of the well 44 from the ambient surroundings. This can include a flexible gasket 46 which extends about the well 44 and cooperates with the body portion 38 and cover 36. The gasket 46 is preferably mounted in a groove 48 defined by the body portion 38 and is engaged by a ring 50 carried on the cover 36.

When the cover is in its second or closed position such as shown in FIG. 4, the ring 50 engages the gasket 46 to seal the well 44 and membrane 34 from the ambient surroundings and to prevent dehydration of the membrane. This also prevents damage to the membrane by physical intrusion or dirt. The ring 50 is preferably provided with a edged surface which bites into the gasket to provide a particularly effective seal.

A retaining means is also provided for releasably retaining the cartridge 14 and its body portion 38 on the housing 12. The retaining means preferably includes a detent 52 on the cartridge 14 which is received in a recess 53 defined by the upper portion 18 of the case 16. The retaining means also preferably includes at least one, and optimally, two wings 54 on the body portion 38 of the cartridge 14 which are received in one or more slots 56 on the case 16. (See, in particular, FIG. 2). The slots 56 are generally perpendicular to the cover 36 so that opening the cover will not disengage the wings 54 from the slots 56.

The upper portion 18 of the case 16 preferably defines a recessed cell 57 (see FIG. 2) into which the cartridge 14 is received. The bottom portion of the cell 57 is defined by a base surface 58. The electrodes 28, 30, and 32 preferably extend upwardly from the base surface 58. The electrodes are preferably mounted within a post 60 which supports the electrodes as they extend upwardly of the base surface 58. The post is preferably generally annular in design with the interior portion thereof filled with an electrically nonconductive support material 62 such as a hardened polyepoxide-containing resin. The electrically nonconductive support material 62 and the top portions of the electrodes define a membrane contact surface 64. The membrane contact surface 64 is preferably generally dome-shaped such that the membrane 34 can be stretched over the contact surface to more effectively place the membrane in operative association with the electrodes.

In order for the sensitivity of the electrode to function properly, electrolyte must be present and maintained between the membrane 34 and the electrodes at the membrane contact surface 64. In prior devices, variations in electrolyte volume from inconsistent osmotic pressure above the membrane could result in loss of full sensitivity or changes in sensitivity owing to variations in the relatively thin electrolyte layer at the membrane-electrode interface 64. Also, mechanical disturbances could cause changes in the electrolyte media at the membrane-electrode interface 64, where the surface of the membrane and that of the electrode support material (i.e., epoxy resin) were both substantially hydrophobic. In the present device, however, this problem is overcome by including a water-swellable coating on the surface of the membrane layer nearest to and covering the electrode as discussed in more detail below. Alternatively, this coating can be applied to the membrane-electrode interface 64, but for convenience, the coating is preferably applied to the disposable and more easily renewable membrane.

The water-swellable coating on the surface of the membrane layer at the membrane contact surface 64 provides a substantially consistent electrolyte volume. This improves the sensitivity of the measurement by about 2:1 over that of prior devices. In addition, less sensitivity drift is seen providing a more stable operation. Unlike prior devices using standard membranes, the device of this invention using the coated membrane provides adequate signals to the sensory microcomputer during start-up procedures.

The body portion 38 preferably also includes a collar 66 which extends opposite of the well 44 with respect to the membrane 34 where it defines the bottom 45 of the well. As shown in FIG. 4, the collar 66 extends about the post 60. The membrane 34 is preferably attached to a retaining surface 65 by an adhesive at the edge of the collar 66 with the portion of the membrane within the collar being free to move. As the cartridge 14 is mounted on the housing 12, the membrane is then stretched over the post 60 providing continuous contact between the membrane 34 and the contact surface 64.

The cover 36 is preferably provided with a closure means 72 such as one or more latches which engage the body portion 38. Generally, the force necessary to disengage the closure means 72 from the body portion 38 should be less than that necessary to disengage the wings 54 from the slots 56. In this manner, the operator can easily open the cover 36 without accidentally disengaging the cartridge 14 from the main housing 12.

The electrodes 28, 30 and 32 together with a support assembly such as the post 60 and the membrane 34 comprise the electrode assembly. In addition, during use the electrode assembly includes means for maintaining osmotic pressure across the membrane 34 as discussed earlier. It is this assembly which is contacted with the body fluid sample for analysis. The electrode assembly 74 is operably associated with the electronic circuit means which analyzes the current from the reaction of the components in the body fluid with the electrodes. The electronic circuit means is in turn operably associated with display means such as a liquid crystal display 76 to indicate amount of glucose in the fluid sample.

Referring to FIG. 5, another embodiment of the electrode assembly 74 is shown wherein the three electrodes 28, 30 and 32 are deposited onto a ceramic surface 66. An electrically nonconductive material 62 is applied as a coating over the electrodes to form an insulating barrier. A portion of each electrode, however, is not coated to form a membrane contact surface 64 so that a membrane can be applied over the electrodes in operative contact therewith.

Figure 6:
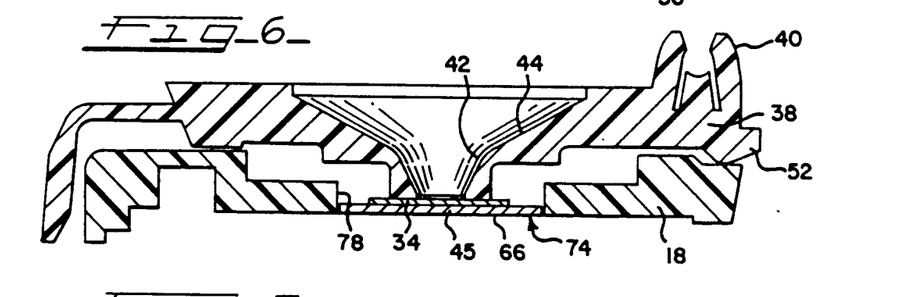
FIG. 6 is a side elevational view showing a device including the electrode assembly of FIG. 5 taken in section along a plane similar to that shown as plane 4—4 of FIG. 1.

FIG. 6 shows the electrode assembly 74 of FIG. 5 in the device. In particular, the electrode assembly including the membrane 34 is positioned within a recess 78 in the base surface 58 of the recessed cell 57. The cartridge 14 is then positioned within the recessed cell as described above whereby the bottom 45 of the well 44 in the body portion 38 of the cartridge contacts the membrane 34. A cover 36 (as shown in FIG. 4) can be attached to the body portion 38 to protect the membrane when the device is not in use.

The three electrode configuration in combination with the osmotic pressure across the membrane and the chemical reactions occurring in the multilayered membrane, its coating and on the electrode make possible consistent electrode behavior and, in particular, performance of the reference electrode that is stable with time. It is well know in the art that silver/silver chloride electrodes provides a stable reference system for electrochemical sensors.

A silver/silver chloride electrode is typically formed by treating a silver surface with an oxidant and chloride ions (such as by treatment with ferric chloride or a neutral hypochlorite solution), by electrochemical plating of chloride ions onto a silver surface or by the mechanical forming of silver and silver chloride by sintering or similar processes.

When this type of electrode is used in a two electrode configuration with the reference cathode, chloride ions will be lost from the reference electrode which eventually leads to unstable electrode behavior. According to the present invention, permanent stable reference electrode behavior is achieved when the hydrogen peroxide produced in the membrane oxidizes the silver metal to silver oxide which is then converted to silver chloride by chloride ion. Advantages include ease of manufacturing of the electrode, self-forming and self-maintaining electrode behavior and long-term reference electrode stability.

The relatively low power needs of the present electrode system, as compared to the relatively high power needs of conventional light reflectance-based methods, permit use of a very compact, lightweight device having an extended battery life. CMOS circuitry is used throughout the device and provides a use-dependent battery life of one to two years.

Figure 7:
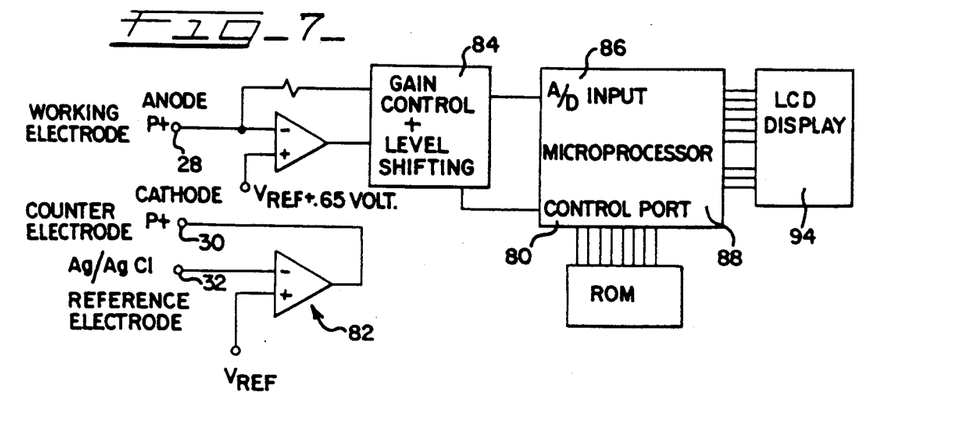
FIG. 7 is a electronic circuit diagram in block form.

A representative electronic circuit for the device is shown in FIG. 7, but other circuits may also be employed. See, for example, Implantable Sensors for Closed Loop Prosthetic Systems, edited by Wen H. Ko, ch. 12, pages 167–175, Futura Publishing Co., Mount Kisco, N.Y. (1985), the noted relevant pages of which are incorporated herein by reference.

During operation of the device, glucose from the blood sample produces a current flow at the working electrode 28. Equal current is provided by a counter electrode 30 in a reference circuit 82. The current is converted in an analog section 84 by a current to voltage converter to a voltage which is inverted, level-shifted and delivered to an Analog/Digital (A/D) converter 86 in the microprocessor 88. As part of the calibration circuit means, the microprocessor can set the analog gain via its control port 90. The A/D converter is activated at one second intervals. The microprocessor looks at the converter output with any number of pattern recognition algorithms known to those skilled in the art until a glucose peak is identified. A timer is then activated for about 30 seconds at the end of which time the difference between the first and last electrode current values is calculated. This difference is then divided by the value stored in the memory during instrument calibration and is then multiplied by the calibration glucose concentration. The glucose value in milligram percent or millimoles per liter is then displayed on the LCD display screen 94.

During this operation sequence, prompts or messages may be displayed on the LCD screen to guide the user through the calibration and sample measurement procedures. In addition, prompts may be displayed to inform the user about necessary maintenance procedures, such as "Replace Sensor" or "Replace Battery." An on/off button 80 initiates the operation and calibration sequences.

As indicated above the membrane is a monolithic homogeneous, multilayered structure including layers formed of materials such as polyethylene, polyvinylchloride, tetrafluoroethylene, polypropylene, cellophane, polyacrylamide, polymethyl methacrylate, silicone polymers, polycarbonate, cuprophane, collagen, polyurethanes and block copolymers thereof.

The layer of the multilayered membrane that is intended to be nearest to and cover the electrode can be coated with a semipermeable water-swellable, substantially solid gel-like film to maintain hydrophilicity at the electrode-membrane interface. This coating also enhances the stability of the third layer of this invention by protecting and supporting the third layer. The electrolyte between a hydrophobic membrane and electrode may experience a large pH gradient due to the electrochemical activity of the electrode, thus damaging the third layer. The buffered electrolyte solution contained in this additional hydrophilic coating adjacent to the third layer protects against such pH-mediated damage. In addition, higher manufacturing yields of usable membranes are achieved by coating the membrane as disclosed herein.

Preferably the coating comprises a flexible water-swellable film having a "dry film" thickness of about 0.1 mil to about 0.5 mil, preferably about 0.25 mil. "Dry film" thickness means the thickness of a cured film cast from a coating formulation onto the surface of the membrane by coating techniques known in the coating arts. The coating formulation comprises a premix of film-forming polymers and a crosslinking agent and is curable upon the application of moderate heat.

Suitable coatings are formed of a curable copolymer of a urethane polymer and a hydrophilic film-forming polymer. Particularly preferred coatings are formed of a polyurethane polymer having anionic carboxylate functional groups and non-ionic hydrophilic polyether segments, which is crosslinked in the present of polyvinylpyrrolidone and cured at a moderate temperature of about 50 degrees C. (about 122 degrees F.).

Particularly suitable for this purpose are aqueous dispersions of fully reacted colloidal polyurethane polymers having cross-linkable carboxyl functionality sold under the trademark BAYBOND by Mobay Corporation, a Bayer U.S.A., Inc. Company, Coatings Division (Pittsburgh, PA). These polymers are supplied in dispersion grades having a polycarbonate—polyurethane backbone containing carboxylate groups identified as XW-121 and XW-123; and a polyester-polyurethane backbone containing carboxylate groups, identified as XW-110-2. A detailed description of the properties of these aqueous polyurethane dispersions can be found in the Technical Summary publication *Baybond Aqueous Polyurethane Dispersions*, published by the Coating Division of Mobay Corporation (undated), the pertinent disclosures of which are incorporated herein by reference.

Particularly preferred is BAYBOND 123, described as an aqueous anionic dispersion of an aliphate polycarbonate urethane polymer and sold as a 35 weight percent solution in water and cosolvent N-methyl-2-pyrrolidone. A description of the properties of BAYBOND 123 is found in the Product Data sheet dated 9/87 and Material Safety Data Sheet dated 9/7/87 published by the supplier and incorporated herein by reference.

Polyvinylpyrrolidone is also particularly preferred as a hydrophilic water-soluble polymer and is available commercially in a range of viscosity grades and range of number average molecular weights from about 18,000 to about 500,000, under the trade designation PVP K homopolymer series by BASF Wyandotte Corporation (Parsippany, NJ) and by GAF Corporation (New York, NY). Particularly preferred is the homopolymer having a number average molecular weight of about 360,000 identified as PVP-K90 by the suppliers, and sold as a powder.

Also suitable are hydrophilic, film-forming copolymers of N-vinylpyrrolidone, such as a copolymer of N-vinylpyrrolidone and vinyl acetate, a copolymer of N-vinylpyrrolidone, ethylmethacrylate and methacrylic acid monomers, and the like.

The polyurethane polymer is crosslinked in the presence of the polyvinylpyrrolidone by preparing a premix of the polymers and adding a cross-linking agent just prior to the production of the membrane. Suitable cross-linking agents can be carbodiimides, epoxides and melamine/formaldehyde resins. Carbodiimide is preferred. A suitable and preferred carbodiimide crosslinker is sold under the trademark UCARLNK XL-25 by Union Carbide Corporation, Solvent Division (Chicago, IL). The properties of this crosslinking agent are found in the product specification brochure titled "UCARLNK XL-25SE in UCAR PM ACETATE."

The flexibility and hardness of the coating can be varied as desired by varying the dry weight solids of the components in the coating formulation. The term "dry weight solids" means the dry weight percent based on the total coating composition after the time the crosslinker is included. A preferred useful coating formulation can contain about 6 to about 20 dry weight percent, preferably about 8 dry weight percent, polyvinylpyrrolidone; about 3 to about 10 dry weight percent preferably about 5 dry weight percent cross-linking agent; and about 70 to about 91 weight percent, preferably about 87 weight percent of a polyurethane polymer, preferably a polycarbonate-polyurethane polymer. The reaction product of such a coating formulation is referred to herein as a water-swellable copolymer of polyurethane and polyvinylpyrrolidone.

In a particularly preferred embodiment, the membrane is a semi-permeable multilayered membrane having at least one layer formed of a nonporous block copolymer having hydrophobic segments (such as silicone polymer segments, aromatic and aliphatic polymer segments, polypropylene oxide segments, polytetramethylene oxide segments and the like) and hydrophilic segments (such as polyoxyethylene segments, polyvinylpyrrolidone segments, polyvinyl alcohol segments and the like) that limits the amount of a substance passing therethrough and a second layer including an enzyme that reacts with the substance to form a product.

The first layer limits the amount of a substance in a fluid that can pass therethrough. The substance can react with the enzyme in the second layer to produce one or more reaction products. A third layer that is permeable to one of the reaction products, but which restricts the passage of other materials can also be used.

The ability of each layer to limit the amount of a molecule that can pass therethrough may be expressed in terms of the moisture-vapor transmission rate (MVTR) and water swelling of the material that forms the layer. As used herein, the MVTR of a material is measured as described in ASTM E 96, the procedure of which is incorporated herein by reference.

The MVTR of the block copolymer of the first layer should be greater than about 4,000 grams per square meter per 24 hours, preferably greater than about 5,000 grams per square meter per 24 hours. The water swelling of this layer should be greater than about 5 percent.

The MVTR of the block copolymer of the third layer should be from about 500 to 4,000 grams per square meter per 24 hours. The above values relate specifically to layers that are employed to measure the amount of glucose in a biological sample. It will be understood that block copolymers having different MVTR values can be used to measure the amounts of other substances in a biological sample and the description of glucose measurement is only illustrative.

The most preferred membranes of this invention are formed of polyurethanes which, of course, include urethane groups and the polyurethane ureas which also include urea groups. The polyurethanes and the polyurethane ureas of the present membrane system are based on poly(oxyalkylene) glycols including poly(oxyethylene) glycol. In accordance with conventional usage, both types of polymers will be referred to herein as polyurethanes.

Membranes of polyurethanes based on poly(oxyalkylene) glycol display no predictable relationship between molecular weight and permeability. The unique separation observed with the present membranes may be explained on the basis of substance-membrane or solute-membrane interactions which tend to affect the partitioning is not due only to the hydrophilic poly(oxyalkylene) glycol or "soft" segment, but the hydrophobic or "hard" segment of the block copolymer also contributes to the overall selectivity.

Thus, by changing the structure of the hydrophobic segment of the block copolymer and/or increasing or decreasing the molecular weight of the poly(oxyalkylene) glycol, the selectivity of the membrane system can be modified. In the membrane system of this invention, for example, the use of two different membranes of block copolyether urethanes based on poly(oxyalkylene) glycol produces the desired selectivity for glucose and hydrogen peroxide.

The preferred poly(oxyalkylene) glycols of this invention include poly(oxyalkylene) glycols, poly(oxytetramethylene) glycols and poly(oxypropylene) glycols. A particularly preferred poly(oxyalkylene) glycol is a poly(oxyethylene) glycol having a weight average molecular weight in the range of about 1,000 to about 4,000.

The organic diisocyanates suitable for use in the preparation of the polyurethanes of the present membranes include 2,4-toluene diisocyanate, 2,6-toluene diisocyanate and 4,4'-diphenylmethane diisocyanate. The use of 4,4'-diphenylmethane diisocyanate is preferred.

Diols useful herein include ethylene glycol, propylene glycol, 1,5-dihydroxypentane, 1,6-dihydroxyhexane, 1,10-dihydroxydecane, 1,4-cyclohexanediol, 1,3-dihydroxyneopentane and alpha, alpha'-dihydroxy-p-xylene.

Diamines useful in the preparation of the polyurethanes described herein include ethylene-diamine, 1,2- (and 1,3-) propanediamine, and methylene-bisochloroaniline.

EXAMPLE 1

The polyurethanes are preferably prepared as block copolymers by solution polymerization techniques as generally described in Lyman, D. J., *J. Polymer Sci.*, 45, 49 (1960). Specifically, a two-step solution polymerization technique is used in which the poly(oxyethylene) glycol is first "capped" by reaction with a diisocyanate to form a macrodiisocyanate. Then the macrodiisocyanate is coupled with a diol (or diamine) and the diisocyanate to form a block copolyetherurethane (or a block copolyurethaneurea). The resulting block copolymers are tough and elastic and may be solution-cast in N,N-dimethylformamide to yield clear films that demonstrate good wet strength when swollen in water.

In particular, a mixture of 8.4 grams (0.006 mole) poly(oxyethylene) glycol (CARBOWAX 1540, Union Carbide Corp., New York, NY) and 3.0 grams (0.012 mole) 4,4'-diphenylmethane diisocyanate in 20 milliliters (ml) dimethyl sulfoxide/4-methyl-2-pentanone (50/50) is placed in a three-necked flask equipped with a stirrer and condenser and protected from moisture. The reaction mixture is stirred and heated at 110 degrees C. (230 degrees F.) for about one hour. To this clear solution is added 1.5 grams (0.014 mole) 1,5-pentanediol and 2.0 grams (0.008 mole) 4,4'-diphenylmethane diisocyanate.

After heating at 110 degrees C. for an additional two hours, the resulting viscous solution is poured into water. The tough, rubbery, white polymer precipitate that forms is chopped in a Waring Blender, washed with water and dried in a vacuum oven at about 60 degrees C. (about 140 degrees F.). The yield is essentially quantitative. The inherent viscosity of the copolymer in N,N-dimethyl formamide is 0.59 at 30 degrees C. (at a concentration of about 0.05 percent by weight).

EXAMPLE 2

A membrane formed of a homogeneous, nonporous block copolymer may be prepared as follows. Polymerization is carried out in a 2-liter glass flask with a detachable top containing five inlets. The inlets provide for nitrogen passage, condenser attachment, stirring, thermometer placing, and ingredient addition. A regulated flow of oxygen-free nitrogen passes from a cylinder, through the apparatus, into a water trap, and to the drain. The contents of the reaction flask are stirred by a Teflon blade connected to an electric motor running at 350 rpm. Air is excluded by a mercury seal. Heat is supplied by an electric mantle and temperature recorded by placing a thermometer in the flask contents. A dropping funnel is used for the addition of ingredients during the reaction.

Thirty grams of dimethylaminoethyl methacrylate and 170 grams of acrylonitrile are used. Potassium persulfate is dissolved in 40 milliliters distilled water and portions of the solution are added in sequence with the foregoing monomers as described in Muier et al., *J. Biomed. Mater. Res.*, 5, 415–445 (1971) which is incorporated herein by reference.

The temperature of the mixture in the flask is maintained at 45–50 degrees C. (113–122 degrees F.) for about 6 hours. The reaction product is an off-white plasticized polymer. The product is washed with water, filtered and dried in a desiccator under vacuum to provide an off-white powder. A typical yield is about 28 grams with a dimethylaminoethyl methacrylate content (as determined from oxygen content analysis) of about 47 percent and an intrinsic viscosity in dimethylformamide at 25 degrees C. (77 degrees F.) of 1.13 dl/g.

The polymer is dissolved in DMF to provide a 10 percent solution by weight. The solution is filtered under vacuum through a Porosity G1 sintered glass funnel and is stored in a desiccator over phosphorus pentoxide for at least 16 hours. The polymer solution is poured onto a glass plate and is spread as a film by passing a doctor blade across the plate. Solvent evaporation is achieved by maintaining a temperature of 45–50 degrees C. for 8 hours in the region of the plate, while solvent vapor is removed by an extractor fan. The membrane is removed from the glass plate by stripping dry or after being soaked with water.

In the enzyme electrode assembly, the membrane layer nearest the anode (the inner layer) comprises a block copolymer, as described above, which is permeable to hydrogen peroxide but which restricts the passage of higher molecular weight substances. This layer has a preferred thickness of less than about 5 microns, more preferably in the range of about 0.1 to about 5 microns and most preferably in the range of about 0.5 to about 3 microns.

The membrane layer nearest the sample (the outer layer) functions as a diffusion barrier to prevent the passage of high molecular weight substances. This layer, also formed of a block copolymer, when used in an electrode assembly to monitor glucose concentrations in a fluid sample, limits the amount of glucose that passes therethrough. This layer has a preferred thickness of less than about 45 microns, more preferably in the range of about 15 to about 40 microns and most preferably in the range of about 20 to about 35 microns.

The second (intermediate) layer that binds the inner and outer layers together includes glucose oxidase, galactose oxidase, uricase or the like combined with a block copolymer of this invention.

The second layer is applied as a thin uniform layer on either the inner or outer membrane layer and the other membrane layer is brought into contact with the second layer to form a multilayered membrane (also referred to as a laminate). The laminate is then dried to cure the enzyme-containing second layer and to bind the layers together.

EXAMPLE 3

The unbound surface of the inner membrane layer intended to be closest to the electrode and to cover the electrode of a multilayered monolithic membrane formed according to the procedure of Example 2 can be coated with a water-swellable film. This example illustrates a coating comprising a polyurethane having anionic carboxylate functional groups and hydrophilic polyether groups and polyvinylpyrrolidone (PVP) that can be cross linked by carbodiimide as follows.

A coating preparation is prepared comprising a premix of a colloidal aqueous dispersion of particles of a urethane polymer having a polycarbonate-polyurethane (PC-PU) backbone containing carboxylate groups and the water-soluble hydrophilic polymer, PVP, which is crosslinked by the addition of the cross-linking agent just before production of the coated membrane. Example coating formulations are illustrated in the following table.

In certain applications, for ease of application in the electrode assembly, an appropriate carrier or frame made of cardboard, rubber or plastic can be secured to the surface of the laminate or multilayered membrane. The frame includes an opening, for example, in the central portion thereof whereby the outer layer of the membrane may be exposed to the electrode.

The electrode assembly of this invention may also be used in the manner commonly employed in the making of amperometric measurements. A sample of the fluid being analyzed is placed in contact with a reference electrode, e.g., silver/silver-chloride, and the electrode of this invention which is preferably formed of platinum. The electrodes are connected to a galvanometer or polarographic instrument and the current is read or recorded upon application of the desired voltage between the electrodes.

The ability of the present device assembly to accurately measure the concentration of substances such as glucose over a broad range of concentrations in fluids including undiluted whole blood samples enables the rapid and accurate determination of the concentration of those substances. That information can be employed in the study and control of metabolic disorders including diabetes.

The foregoing is intended as illustrative of the present invention but is not limiting. It should be understood that numerous variations and modifications can be made without departing from the spirit and scope of the novel

| PREMIX | A WEIGHT | A DRY WEIGHT PERCENT SOLIDS | B WEIGHT | B DRY WEIGHT PERCENT SOLIDS | C WEIGHT | C DRY WEIGHT PERCENT SOLIDS |
|---|---|---|---|---|---|---|
| 1. PVP (Note 1) | 48 | 6 | 64 | 8 | 160 | 20 |
| 2. PC-PV (Note 2) | 260 | 91 | 248 | 87 | 200 | 70 |
| CROSS-LINKING AGENT | | | | | | |
| 3. Carbodiimide (Note 3) | 6 | 3 | 10 | 5 | 20 | 10 |
| Totals | 314 | 100 | 322 | 100 | 380 | 100 |

Note 1: Aqueous solution containing 12.5 weight percent PVP prepared from Polyvinylpyrrolidone having a number average molecular weight of about 360,000 sold as a powder under the trademark BASF K-90 by BASF Wyandotte Corporation (Parsippany, NJ).
Note 2: Colloidal dispersion of a polycarbonate-polyurethane (PC-PU) polymer at about 35 weight percent solids in a cosolvent mixture of about 53 weight percent water and about 12 weight percent N-methyl-2-pyrrolidone sold under the trademark BAYBOND 123 (or XW-123) by Mobay Corporation, Coatings Division (Pittsburgh, PA). As supplied, the dispersion has a pH of about 7.5-9.0.
Note 3: Carbodiimide sold under the trademark UCARLNK XL-25SE by Union Carbide Corporation, Solvent Division (Chicago, IL) supplied at about 50 weight percent solids in a solvent solution of propylene glycol monomethylether acetate.

The viscosity and pH of the premix can be controlled and maintained during processing and to prolong the pot life by adding water or adjusting the pH with dilute ammonia solution or an equivalent base prior to adding the crosslinker.

For production, the coating is applied with a Mayer rod into the unbound surface of a multilayered membrane that constitutes the inner layer described in Example 2. The amount of coating applied should cast a film having a "dry film" thickness of about 0.1 mil to about 0.5 mil, preferably about 0.25 mil. The coating is dried above room temperature preferably at about 50 degrees centigrade.

This coating dries to a substantially solid gel-like film that is water swellable to maintain electrolyte between the membrane covering the electrode and the electrode in the electrode assembly during use.

concept of the invention.

What is claimed is:

1. A biological fluid measuring device comprising:
   (a) a main housing including electronic circuit means associated with at least two electrodes;
   (b) a disposable cartridge having a homogeneous, monolithic membrane and being removably mounted on the housing with the membrane operably associated with the electrodes, the cartridge including means for protecting the membrane when not in use and means for maintaining the membrane in operative association with the electrodes at the electrode-membrane interface by osmotic pressure during storage and use, the maintaining means including an osmotic agent which does not permeate the membrane; and (c) means for supporting the electrodes so that the supporting means, the electrodes, the maintaining means and the membrane are in operative contact to provide an electrode assembly.

2. The biological fluid measuring device of claim 1 wherein the maintaining means is a liquid that applies an osmotic pressure across the membrane of about 30–90 millimeters mercury column height under ambient room temperature and pressure.

3. The biological fluid measuring device of claim 1 wherein the osmotic agent is a water-soluble polymer having a weight average molecular weight between about 800 and about 20,000.

4. The biological fluid measuring device of claim 1 wherein the cartridge includes a body portion retaining the membrane and the protection means includes a cover movably mounted on the body portion.

5. The biological fluid measuring device of claim 4 wherein the cartridge includes a hinge for mounting the cover on the body portion.

6. The biological fluid measuring device of claim 4 wherein the body portion and membrane define a well having sides and a bottom with the bottom being defined at least in part, by the membrane.

7. The biological fluid measuring device of claim 6 wherein the well has a volume of less than about 0.2 cubic centimeters and is adapted to accept a sample as small as about 5 microliters.

8. The biological fluid measuring device of claim 1 wherein the protection means seals the membrane from ambient air.

9. The biological fluid measuring device of claim 8 wherein the protection means includes a flexible gasket.

10. The biological fluid measuring device of claim 1 further including retaining means for releasably retaining the cartridge on the housing.

11. The biological fluid measuring device of claim 10 wherein the retaining means includes a detente on the cartridge that is received in a recess defined by the housing.

12. The biological fluid measuring device of claim 1 wherein the housing defines a base surface with the electrode projecting upwardly of the base surface.

13. The biological fluid measuring device of claim 12 wherein the membrane is stretched over the electrode-membrane interface.

14. The biological fluid measuring device of claim 1 wherein the membrane includes a first layer of nonporous block copolymer having hydrophobic segments and hydrophilic segments that limits the amount of the substance passing therethrough, a second layer of a nonporous block copolymer including an enzyme bound to the first layer, said enzyme reacting with the substance to form a product, and a third layer of a nonporous block copolymer having hydrophobic and hydrophilic segments that is bound to the second layer, the third layer having a water-swellable coating on the unbound surface intermediate to the electrode and covering the surface of the electrode, so that the third layer restricts the passage of the substance therethrough but permits the passage of the product and the intermediate coating maintains electrolyte at the membrane-electrode interface whereby the measurable amount of product formed corresponds to the amount of the substance in the sample.

15. The biological fluid measuring device of claim 1 further including display means carried by the main housing and operably associated with the electronic circuit means for displaying a result.

16. A biological fluid measuring device comprising:
(a) a case having an upper portion and a lower portion together defining a cavity, the upper portion also defining a recessed cell having a base surface;
(b) at least two electrodes mounted on the upper portion of the case and extending upwardly from the base surface;
(c) electronic circuit means carried by the case within the cavity and operably associated with the electrodes for processing a signal from the electrodes;
(d) display means carried by the case and operably associated with the electronic circuit means for displaying a result;
(e) a disposable cartridge having a body portion defining a receiving surface, the cartridge also including a homogeneous, monolithic membrane mounted on the receiving surface, means for maintaining the membrane in operative association with the electrodes by osmotic pressure at the electrode-membrane interface during storage and use, the maintaining means including an osmotic agent which does not permeate the membrane, and a cover movably mounted on the body portion, the body portion being removably mounted in the recessed cell of the upper portion of the case with the membrane operably associated with the electrodes; and
(f) means for supporting the electrodes so that the supporting means, the electrodes, the maintaining means and the membrane are in operative contact to provide an electrode assembly.

17. The biological fluid measuring device of claim 16 wherein the maintaining means is a liquid comprising an osmotic agent capable of applying an osmotic pressure of about 30–90 millimeters mercury column height at ambient room temperature and pressure.

18. The biological fluid measuring device of claim 16 wherein the cartridge includes a hinge which movably mounts the cover on the body portion.

19. The biological fluid measuring device of claim 16 wherein the body portion and membrane define a well that is adapted to receive the biological fluid.

20. The biological fluid measuring device of claim 16 including an electrically nonconductive support material, the electrodes and electrically nonconductive support material defining a membrane contact surface.

21. The biological fluid measuring device of claim 16 wherein the membrane is stretched over the electrode-membrane interface.

22. The biological fluid measuring device of claim 16 including a gasket about the well cooperating with the body portion and cover to seal the well from ambient air.

23. The biological fluid measuring device of claim 16 wherein the electrodes are carried by a post mounted on the upper portion of the case and extending upwardly of the base surface.

24. The biological fluid measuring device of claim 23 wherein the body portion includes a collar which extends about the post, the membrane being attached to the collar.

25. The biological fluid measuring device of claim 23 wherein the post includes an electrically nonconductive support material to retain the electrodes in a fixed position.

26. A biological fluid measuring device comprising:

(a) a case defining a cavity;

(b) at least two electrodes mounted on the case;

(c) means for supporting the electrodes;

(d) electronic circuit means carried in the cavity and operably associated with the electrodes for processing a signal from the electrodes;

(e) display means carried by the case and operably associated with the electronic circuit means;

(f) a body portion defining an opening being removably mounted on the case;

(g) a homogeneous, monolithic membrane mounted on the body portion and being operably associated with the electrodes; means for maintaining the membrane in association with the electrodes by osmotic pressure at the electrode-membrane interface including an osmotic agent that does not permeate the membrane whereby the supporting means, the electrodes, the maintaining means and the membrane are in operative contact during use to provide an electrode assembly, the membrane and the opening together defining a well; and (h) a cover movably mounted on one of the case and body portion, the cover having a first position which permits access to the well and a second position which protects the well from the ambient surroundings.

27. The biological fluid measuring device of claim 26 wherein the maintaining means is a liquid comprising an osmotic agent capable of applying a pressure of about 30-90 millimeters mercury column height across the membrane under ambient room temperature and pressure.

28. The biological fluid measuring device of claim 26 including a gasket carried by one of the cover and body portion for sealing with the cover and body portion to protect the well when the cover is in its second position.

29. A cartridge for use as part of a biological fluid measuring device having a housing carrying electronic circuit means and at least two electrodes, the cartridge comprising:

(a) a body portion having a side wall defining an opening;

(b) a homogeneous, monolithic membrane mounted on the body portion across the opening, whereby the sidewall and membrane together define a well, the well including means received above and in contact with the membrane for maintaining the membrane in operative association with the electrode by osmotic pressure at the electrode-membrane interface during storage and use, the maintaining means including an osmotic agent which does not permeate the membrane;

(c) means for mounting the body portion on the housing with the membrane operably associated with the electrode; and (d) a cover movably mounted on the body portion and having a first position which permits access to the well and the second position which protects the well from the ambient surroundings.

30. The cartridge of claim 29 further including a hinge for movably mounting the cover on the body portion.

31. The cartridge of claim 29 further including a gasket and cooperating with the cover and body portion to seal the well from the ambient surroundings when the cover is in its second position.

32. The cartridge of claim 29 wherein the gasket is carried by the body portion and extends about the well, and the cover includes a ring which engages the gasket when the cover is in its second position.

33. The cartridge of claim 29 wherein the body portion includes a collar opposite the well with respect to the portion of the membrane which defines the well, the membrane being attached to the collar.

34. The cartridge of claim 29 wherein the body portion includes at least one wing which engages a slot defined by the housing.

35. A biological fluid measuring device comprising:

(a) a working electrode;

(b) a counter electrode;

(c) a reference electrode;

(d) a homogeneous, monolithic membrane maintained in operable association with the working electrode, counter electrode and reference electrode by osmotic pressure means at the membrane-electrode interface, the osmotic pressure means including an osmotic agent which does not permeate the membrane;

(e) means for supporting the working electrode, the counter electrode and the reference electrodes so that each electrode is in operative contact with the membrane to provide an electrode assembly;

(f) processing circuit means operably associated with the working electrode and the counter electrode for analyzing the current at the working electrode and counter electrode when a body fluid is placed on the membrane;

(g) calibration circuit means operably associated with the working electrode and counter electrode and the processing circuit means for calibrating the processing circuit means when a reference solution is placed on the membrane; and (h) display means operably associated with the processing circuit means for displaying a result.

36. The biological fluid measuring device of claim 35 wherein the working electrode is anodic and the counter electrode is cathodic.

37. The biological fluid measuring device of claim 35 wherein the counter electrode is anodic and the working electrode is cathodic.

38. The biological fluid measuring device of claim 35 wherein the osmotic pressure means is a liquid capable of applying about 30-90 millimeters mercury column pressure under ambient room temperature and pressure.

39. A device for determining the amount of a substance in a biological fluid comprising:

(a) a main housing including electronic circuit means associated with at least two electrodes;

(b) a disposable cartridge having a homogeneous, monolithic membrane and being removably mounted on the housing with the membrane operably associated with the electrodes, the cartridge including means for protecting the membrane when not in use and means for maintaining the membrane in operative association with the electrodes at the electrode-membrane interface by osmotic pressure during storage and use; and (c) means for supporting the electrodes so that the supporting means, the electrodes, the maintaining means and the membrane are in operative contact to provide an electrode assembly wherein the amount of substance in the biological fluid can be determined without dilution or pretreatment of the fluid.

40. The biological fluid measuring device of claim 39 wherein the maintaining means is a liquid that applies an osmotic pressure across the membrane of about 30–90 millimeters mercury column height under ambient room temperature and pressure.

41. The biological fluid measuring device of claim 39 wherein the maintaining means includes an osmotic agent comprising a water-soluble polymer having a weight average molecular weight between about 800 and about 20,000.

42. The biological fluid measuring device of claim 39 wherein the cartridge includes a body portion retaining the membrane and the protection means includes a cover movably mounted on the body portion.

43. The biological fluid measuring device of claim 42 wherein the cartridge includes a hinge for mounting the cover on the body portion.

44. The biological fluid measuring device of claim 42 wherein the body portion and membrane define a well having sides and a bottom with the bottom being defined at least in part by the membrane.

45. The biological fluid measuring device of claim 44 wherein the well has a volume of less than about 0.2 cubic centimeters and is adapted to accept a sample as small as about 5 microliters.

46. The biological fluid measuring device of claim 39 wherein the protection means seals the membrane from ambient air.

47. The biological fluid measuring device of claim 46 wherein the protection means includes a flexible gasket.

48. The biological fluid measuring device of claim 39 further including retaining means for releasably retaining the cartridge on the housing.

49. The biological fluid measuring device of claim 48 wherein the retaining means includes a detente on the cartridge that is received in a recess defined by the housing.

50. The biological fluid measuring device of claim 39 wherein the housing defines a base surface with the electrode projecting upwardly of the base surface.

51. The biological fluid measuring device of claim 50 wherein the membrane is stretched over the electrode-membrane interface.

52. The biological fluid measuring device of claim 39 further including display means carried by the main housing and operably associated with the electronic circuit means for displaying a result.

53. A device for determining the amount of a substance in a biological fluid comprising:
(a) a case having an upper portion and a lower portion together defining a cavity, the upper portion also defining a recessed cell having a base surface;
(b) at least two electrodes mounted on the upper portion of the case and extending upwardly from the base surface;
(c) electronic circuit means carried by the case within the cavity and operably associated with the electrodes for processing a signal from the electrodes;
(d) display means carried by the case and operably associated with the electronic circuit means for displaying a result;
(e) a disposable cartridge having a body portion defining a receiving surface, the cartridge also including a homogeneous, monolithic membrane mounted on the receiving surface, means for maintaining the membrane in operative association with the electrodes by osmotic pressure at the electrode-membrane interface during storage and use and a cover movably mounted on the body portion, the body portion being removably mounted in the recessed cell of the upper portion of the case with the membrane operably associated with the electrodes; and
(f) means for supporting the electrodes so that the supporting means, the electrodes, the maintaining means and the membrane are in operative contact to provide an electrode assembly wherein the amount of substance in the biological fluid can be determined without dilution or pretreatment of the fluid.

54. The biological fluid measuring device of claim 53 wherein the cartridge includes a hinge which movably mounts the cover on the body portion.

55. The biological fluid measuring device of claim 53 wherein the body portion and membrane define a well that is adapted to receive the biological fluid.

56. The biological fluid measuring device of claim 53 including an electrically nonconductive support material, the electrodes and electrically nonconductive support material defining a membrane contact surface.

57. The biological fluid measuring device of claim 53 wherein the membrane is stretched over the electrode-membrane interface.

58. The biological fluid measuring device of claim 53 including a gasket about the well cooperating with the body portion and cover to seal the well from ambient air.

59. The biological fluid measuring device of claim 53 wherein the electrodes are carried by a post mounted on the upper portion of the case and extending upwardly of the base surface.

60. The biological fluid measuring device of claim 59 wherein the body portion includes a collar which extends about the post, the membrane being attached to the collar.

61. The biological fluid measuring device of claim 59 wherein the post includes an electrically nonconductive support material to retain the electrodes in a fixed position.

62. A device for determining the amount of a substance in a biological fluid comprising:
(a) a case defining a cavity;
(b) at least two electrodes mounted on the case;
(c) means for supporting the electrodes;
(d) electronic circuit means carried in the cavity and operably associated with the electrodes for processing a signal from the electrodes;
(e) display means carried by the case and operably associated with the electronic circuit means;
(f) a body portion defining an opening being removably mounted on the case;
(g) a homogeneous, monolithic membrane mounted on the body portion and being operably associated with the electrodes; means for maintaining the membrane in association with the electrodes by osmotic pressure at the electrode-membrane interface so that the supporting means, the electrodes, the pressure means and the membrane are in operative contact during use to provide an electrode assembly, the membrane and the opening together defining a well; and
(h) a cover movably mounted on one of the case and body portion, the cover having a first position which permits access to the well and a second position which protects the well from the ambient surroundings wherein the amount of substance in the biological fluid can be determined without dilution or pretreatment of the fluid.

63. The biological fluid measuring device of claim 62 including a gasket carried by one of the cover and body portion for sealing with the cover and body portion to protect the well when the cover is in its second position.

64. A cartridge for use as part of a device for determining the amount of a substance in a biological fluid having a housing carrying electronic circuit means and at least two electrodes, the cartridge comprising:
 (a) a body portion having a side wall defining an opening;
 (b) a homogeneous, monolithic membrane mounted on the body portion across the opening, whereby the sidewall and membrane together define a well, the well including means received above and in contact with the membrane for maintaining the membrane in operative association with the electrode by osmotic pressure at the electrode-membrane interface during storage and use;
 (c) means for mounting the body portion on the housing with the membrane operably associated with the electrode; and
 (d) a cover movably mounted on the body portion and having a first position which permits access to the well and the second position which protects the well from the ambient surroundings wherein the amount of substance in the biological fluid can be determined without dilution or pretreatment of the fluid.

65. The cartridge of claim 64 further including a hinge for movably mounting the cover on the body portion.

66. The cartridge of claim 64 further including a gasket and cooperating with the cover and body portion to seal the well from the ambient surroundings when the cover is in its second position.

67. The cartridge of claim 64 wherein the gasket is carried by the body portion and extends about the well, and the cover includes a ring which engages the gasket when the cover is in its second position.

68. The cartridge of claim 64 wherein the body portion includes a collar opposite the well with respect to the portion of the membrane which defines the well, the membrane being attached to the collar.

69. The cartridge of claim 64 wherein the body portion includes at least one wing which engages a slot defined by the housing.

70. A device for determining the amount of a substance in a biological fluid comprising:
 (a) a working electrode;
 (b) a counter electrode;
 (c) a reference electrode;
 (d) a homogeneous, monolithic membrane maintained in operable association with the working electrode, counter electrode and reference electrode by osmotic pressure means at the membrane-electrode interface;
 (e) means for supporting the working electrode, the counter electrode and the reference electrodes so that each electrode is in operative contact with the membrane to provide an electrode assembly;
 (f) processing circuit means operably associated with the working electrode and the counter electrode for analyzing the current at the working electrode and counter electrode when a body fluid is placed on the membrane;
 (g) calibration circuit means operably associated with the working electrode and counter electrode and the processing circuit means for calibrating the processing circuit means when a reference solution is placed on the membrane; and
 (h) display means operably associated with the processing circuit means for displaying a result wherein the amount of substance in the biological fluid can be determined without dilution or pretreatment of the fluid.

71. The biological fluid measuring device of claim 70 wherein the working electrode is anodic and the counter electrode is cathodic.

72. The biological fluid measuring device of claim 70 wherein the counter electrode is anodic and the working electrode is cathodic.

* * * * *

UNITED STATES PATENT AND TRADEMARK OFFICE
CERTIFICATE OF CORRECTION

PATENT NO. : 4,994,167
DATED : February 19, 1991
INVENTOR(S) : Shults et al.

It is certified that error appears in the above-identified patent and that said Letters Patent is hereby corrected as shown below:

Column 3, line 40, change "a" to --as--.

Column 15, lines 31-32, change "methylene-bis-ochloroaniline" to --methylene-bis-o-chloroaniline--.

Signed and Sealed this

First Day of December, 1992

Attest:

DOUGLAS B. COMER

Attesting Officer

Acting Commissioner of Patents and Trademarks